United States Patent [19]
Hayakawa et al.

[11] Patent Number: 6,054,262
[45] Date of Patent: Apr. 25, 2000

[54] METHOD FOR CONTROLLING CULTURE OF LACTIC BACTERIA

[75] Inventors: Kazuhito Hayakawa; Katsuhisa Harada; Sogo Takeuchi; Shinya Shibata; Akihiko Miyagi, all of Tokyo, Japan

[73] Assignee: Kabushiki Kaisha Yakult Honsha, Tokyo, Japan

[21] Appl. No.: 09/000,144

[22] PCT Filed: Jul. 25, 1996

[86] PCT No.: PCT/JP96/02093

§ 371 Date: May 13, 1998

§ 102(e) Date: May 13, 1998

[87] PCT Pub. No.: WO97/05236

PCT Pub. Date: Feb. 13, 1997

[30] Foreign Application Priority Data

Jul. 31, 1995 [JP] Japan ................................. 7-214154

[51] Int. Cl.[7] .............................. C12Q 1/02; C12Q 1/24; C12P 7/56
[52] U.S. Cl. .................................. 435/4; 435/30; 435/139
[58] Field of Search .................................. 435/139, 30, 4

[56] References Cited

PUBLICATIONS

Paul Fairbrother, et al., "Whey fermentation: on–line analysis of lactose and lactic acid by FTIR spectroscopy", Applied Microbiology & Biotechnology, (1991) p. 301–305.

Robert L. White, et al., Fourier transform infrared detection of Pyruic acid assimilation by *E. coli*, Anal. Chem. (1985)p. 2487–2491.

*Primary Examiner*—Herbert J. Lilling
*Attorney, Agent, or Firm*—Oblon, Spivak, McClelland, Maier & Neustadt, P.C.

[57] ABSTRACT

A novel method for controlling culture of lactic bacteria, which enables the state of bacteria to be controlled in a simple and rapid manner in the step of cultivation in the production of various products utilizing lactic bacteria. The method is characterized in that, in the step of cultivating lactic bacteria, the intensity of the infrared absorption assignable to dissociable lactic acid and that of the infrared absorption assignable to nondissociable lactic acid in the culture are measured by FT-IR spectrometry and the pH value of the culture and/or the lactic acid concentration of the culture are calculated based on the measurements. The method according to another embodiment is characterized in that, in the above method for controlling culture of lactic bacteria, the intensity of the infrared absorption assignable to glucose as a substrate or an alcoholic C-O group of lactose is measured and the glucose concentration or lactose concentration is calculated based on these measurements. The method according to a further embodiment is characterized in that the intensity of the infrared absorption is measured in-line by the ATR-FT-IR spectrometry and, based on the measurements, the state of culture of lactic bacteria is automatically monitored and controlled.

3 Claims, 9 Drawing Sheets

METHOD FOR CONTROLLING CULTURE OF LACTIC BACTERIA

TECHNICAL FIELD

The present invention relates to a method for controlling culture of lactic bacteria in the step of cultivation in the production of various products utilizing lactic bacteria; more specifically, the present invention relates to a method for controlling the step of culture of lactic bacteria particularly utilizing the ATR-FT-IR spectrometry, particularly a novel method for controlling culture of lactic bacteria, which enables the state of culture of lactic bacteria to be monitored and controlled in a simple and rapid manner, by employing the concentration of glucose or lactose as a substrate, the concentration of lactic acid as a culture product of lactic bacteria, and the acidity and the pH value of a fermented liquid as indexes.

TECHNICAL BACKGROUND

Generally, in the production of various products utilizing lactic bacteria such as fermented milk, a method for controlling a fermentation of the culture, namely, a method for investigating the state of the fermentation proceeded and determining the completion of the fermentation, is carried out by employing the concentration of a saccharide as a substrate, the concentration of lactic acid as a product formed following fermentation, and values of the acidity and the pH value of a fermented liquid, as indexes in the control of the step of culture. In order to obtain these values, conventionally a fermented liquid has been sampled once at a proper step, and then have been analyzed quantitatively regarding each item according to an ordinary procedure, utilizing, for example, a neutralization titration method. According to such a method, however, there occurs a problem of a large accidental error in titration for measuring each index value; in addition, since much time and many hands are required, it has not been possible to control the step of cultivation in a simple and rapid manner.

Moreover, recently there have been found examples investigating a possibility of a method of more reliable and simple on-line measurement; however, they are only for obtaining basic knowledge about on-line measurement in the step of the fermentation of specific products and are still matters of basic investigation; and no example actually investigating whether it is possible or not to control the step of cultivation of lactic bacteria according to such methods of measurement has been reported, and hence it has been desired keenly in the field concerned to develop a new method for controlling the step of cultivation of lactic bacteria utilizing a method of more reliable and simple measurement.

As described above, it has been desired keenly to develop a method for measuring the concentration of a saccharide, the concentration of lactic acid, acidity and a pH value as indexes for controlling the state of culture of lactic bacteria in a rapid, simple and precise manner, particularly, to develop a method of in-line measurement and a method for controlling culture of lactic bacteria based thereon.

The present inventors have engaged in assiduous studies with a view to developing such a new method for controlling culture of lactic bacteria, and as a result have found that the infrared absorption spectrum of a fermented liquid is measured by the FT-IR spectrometry (Fourier transform infrared spectroscopy) and that of the infrared absorption assignable to dissociable lactic acid, the intensity of the infrared absorption assignable to nondissociable lactic acid in the culture, the intensity of the infrared absorption assignable to an alcoholic C-O group of glucose and the intensity of the infrared absorption assignable to an alcoholic C-O group of lactose are measured, and the lactic acid concentration, the pH value, the glucose concentration and the lactose concentration of the culture can be measured based on these measurements and that the state of culture of lactic bacteria can be monitored and controlled in a simple and rapid manner, by employing these measurements as indexes, which has led to the completion of the present invention. In addition, they have found that, of FT-IR methods, the ATR-FT-IR spectrometry, a method for measuring a whole reflective spectrum, enables the numerical values of various indexes to be measured and, based on the measurements, the culture of lactic bacteria is automatically controlled.

SUMMARY OF THE INVENTION

It is the objective of the present invention to provide a novel method for controlling culture of lactic bacteria, which enables the state of culture of lactic bacteria to be controlled in a simple and rapid manner in the step of cultivation in the production of various products utilizing lactic bacteria.

The present invention relates to a method for controlling culture of lactic bacteria, characterized in that the method comprises measuring, in the step of cultivating lactic bacteria, the intensity of the infrared absorption assignable to dissociable lactic acid and that of the infrared absorption assignable to nondissociable lactic acid in the culture by the FT-IR spectrometry, and calculating the pH value of the culture and/or the lactic acid concentration of the culture according to these measurements. The method according to another embodiment is a method for controlling culture of lactic bacteria, characterized in that, in the above method for controlling culture of lactic bacteria, the intensity of the infrared absorption assignable to an alcoholic C-O group of glucose or lactose as a substrate is measured and the glucose concentration or the lactose concentration is calculated based on these measurements; and the method according to a further embodiment is a method for controlling culture of lactic bacteria, characterized in that the intensity of the infrared absorption is measured in-line by the ATR-FT-IR spectrometry and, based on the measurements, the state of culture of lactic bacteria is automatically monitored and controlled.

According to the present invention, it becomes possible, in the production of products utilizing lactic bacteria such as fermented milk, to measure various index values needed for controlling the step of cultivation in a rapid, simple and precise manner, and, based on the measurements, the state of culture of lactic bacteria in the step of cultivation can be monitored and controlled in a simple and rapid manner. Besides, the above various index values can be measured in-line by the ATR-FT-IR spectrometry and the step of culture of lactic bacteria can be controlled automatically.

DISCLOSURE OF THE INVENTION

It is an objective of the present invention to provide a method for controlling the step of culture in the production of various products utilizing lactic bacteria such as fermented milk.

It is another objective of the present invention to provide a novel method for controlling culture of lactic bacteria, which enables various index values controlling culture to be measured in a rapid and simple manner in the step of culture of lactic bacteria and the state of culture of lactic bacteria to be monitored and controlled in a simple and rapid manner.

It is still another objective of the present invention to provide a method for controlling culture of lactic bacteria automatically in a simple and rapid manner by measuring the above index values particularly in-line in the above step of cultivating lactic bacteria;

The present invention dissolving the above problems is a method for controlling culture of lactic bacteria, characterized in that the method comprises measuring, in the step of cultivating lactic bacteria, the intensity of the infrared absorption assignable to dissociable lactic acid and that of the infrared absorption assignable to nondissociable lactic acid in the culture by the FT-IR spectrometry, and calculating the pH value of the culture and/or the lactic acid concentration of the culture according to these measurements.

In addition, the method according to another embodiment is a method for controlling culture of lactic bacteria, characterized in that, in the above method for controlling culture of lactic bacteria, the intensity of the infrared absorption assignable to an alcoholic C-O group of glucose or lactose as a substrate is measured and the glucose concentration or the lactose concentration is calculated based on these measurements. The method according to a further embodiment is a method for controlling culture of lactic bacteria, characterized in that the intensity of the infrared absorption is measured in-line by the ATR-FT-IR spectrometry. The method according to a further embodiment is a method for controlling culture of lactic bacteria, characterized in that the intensity of the infrared absorption assignable to dissociable lactic acid is the intensity of the infrared absorption at about 1575 cm$^{-1}$ and the intensity of the infrared absorption assignable to nondissociable lactic acid is the intensity of the infrared absorption at about 1725 cm$^{-1}$. Further, the method according to a further embodiment is a method for controlling culture of lactic bacteria, characterized in that the intensity of the infrared absorption assignable to an alcoholic C-O group of glucose is the intensity of the infrared absorption at about 1080 cm$^{-1}$ or about 1035 cm$^{-1}$ and the intensity of the infrared absorption assignable to an alcoholic C-O group of lactose is the intensity of the infrared absorption at about 1075 cm$^{-1}$ or about 1042 cm$^{-1}$.

The wave-numbers specified here include a range of about±10 cm$^{-1}$.

Next, the present invention will be described in more detail.

Lactic bacteria according to the present invention are dairy lactic bacteria generally utilized for the dairy industry, and, for example, lactic bacteria such as the Lactobacillus genus, the streptococcus genus, the Lactococcus genus and the Leuconostoc genus can be exemplified as typical ones; in addition, bacteria capable of controlling cultivation similarly with the saccharide concentration, the lactic acid concentration and a pH value capable of being measured according to the method of the present invention as indexes are included naturally in lactic bacteria according to the present invention as ones capable of being utilized in the same manner, and examples thereof include the Bifidobacterium genus, the Pediococcus genus and the Sporolactobacillus genus.

The step of culture of lactic bacteria according to the present invention typically means the step of fermentation of various products utilizing lactic bacteria such as fermented milk; however, steps of fermentation and cultivation including lactic bacteria such as the step of cultivation aiming at culture of lactic bacteria themselves are targeted irrespective of kind.

The FT-IR (Fourier transform infrared spectroscopy) spectrometry, particularly the ATR (attenuated total reflection)-FT-IR spectrometry described herein comprises introducing light of the infrared region from a sample into a light interference meter, measuring the intensity of light coming therefrom as a function of the moving distance of a movable mirror and obtaining a spectrum by the Fourier transform; in particular, the ATR-FT-IR spectrometry is a method known as spectrometry measuring the change of the intensity of the whole reflected light when the angle of incidence of light with a constant wavelength is changed.

The in-line method according to the present invention means a method for measuring data by fixing a probe (sensor part) of an infrared absorption spectrum measuring device according to the present invention directly to a culture tank for performing culture of lactic bacteria, which enables the data to be measured directly by the culture tank without employing a step of performing sampling once during the cultivation of lactic bacteria as in a conventional method. Moreover, it is substantially discriminated from an indirect method guessing the lactic acid concentration from the measurement of the amount of consumption of a substrate such as lactose and glucose as in a conventional method.

In the present invention, the infrared absorption spectrum of a culture broth of lactic bacteria aiming at controlling a fermentation of the culture was measured by the FT-IR spectrometry, and the correlation between the intensity of a specific wave-number and values such as the glucose concentration, the lactose concentration, the lactic acid concentration, acidity and a pH value was examined specifically.

It has been revealed as a result of it that there exists a strong correlation (coefficient of correlation: 0.999) between the glucose concentration and the absorption intensity assignable to an alcoholic C-o group of glucose at 1080 cm$^{-1}$ or 1035 cm$^{-1}$ according to a test employing an aqueous glucose solution as a standard liquid (see FIG. 1 and FIG. 2). Besides, it has been revealed that, also in the case of performing measurement in-line by fixing a probe of an infrared absorption spectrum measuring device directly to a fermentation tank for culturing lactic bacteria, there exist strong correlations at respective wave-numbers (coefficient of correlation: 0.992 at 1080 cm$^{-1}$, 0.998 at 1035 cm$^{-1}$), and that the glucose concentration can be measured from the intensity of the IR absorption (see FIG. 5).

Next, it has been revealed that there exists a strong correlation (coefficient of correlation: 0.998) between the lactose concentration and the absorption intensity assignable to an alcoholic C-O group of lactose at 1075 cm$^{-1}$ or 1042 cm$^{-1}$ according to a test employing an aqueous lactose solution as a standard liquid (see FIG. 3). Besides, it has been revealed that, also in the case of performing measurement in-line by fixing a probe of an infrared absorption spectrum measuring device directly to a fermentation tank for culturing lactic bacteria, there exist strong correlations at respective wave-numbers (coefficient of correlation: 0.995 at 1075 cm$^{-1}$, 0.998 at 1042 cm$^{-1}$), and that the lactose concentration can be measured from the intensity of the IR absorption (see FIG. 6).

Next, it has been revealed that there exists an excellent correlation between the lactose concentration and the absorption intensity assignable to a C=O group of carboxylic acid at 1725 cm$^{-1}$, the absorption intensity assignable to a C-O group of carboxylic acid at 1237 cm$^{-1}$ and the absorption intensity assignable to an alcoholic C-O group at 1132 cm$^{-1}$ according to a test employing an aqueous lactic acid solution as a standard liquid (see FIG. 4); however, in the case of performing measurement in-line by fixing a probe directly to a fermentation tank, there is observed no linear relation between the absorption intensity of any wave-number and the lactic acid concentration. Hence, it has been found as a result of investigating this point variously that the lactic acid concentration can be calculated by taking note of the dissociation ratio of lactic acid and employing the double regression method combining the intensity of the infrared absorption assignable to dissociable lactic acid and the intensity of the infrared absorption assignable to nondissociable lactic acid. Moreover, it has been found as a simpler method of calculation that the lactic acid concentration can be calculated by performing an amendment on a ratio of depth of creeping into a measuring sample, a function of a wave-number of infrared rays, at each intensity in the ATR spectrometry.

Moreover, it has been found that acidity and a pH value can be calculated precisely from the dissociation ratio of lactic acid by applying the Henderson-Hasselbalch equation.

That is, an explanation will be made employing Example 1 to be described later as an example; in the case that the pH when the dissociation ratio of an electrolyte is 50% is made pKa, the dissociation ratio (%) is as below by varying the Henderson-Hasselbalch equation, pH=pKa+log [dissociation concentration]/[nondissociation concentration]:

dissaciation ratio=$\{10^{(pH-pKa)}/(10^{(pH-pKa)}+1)\} \times 100$; and since pKa of lactic acid is 3.86, the relation between the pH and the dissociation ratio is as below:

dissociaton ratio=$\{10^{(pH-3.86)}(10^{(pK-3.86)}+1)\} \times 100$. Since the pH in the step of cultivation in the logosa medium in Example 1 to be described later is varied to from 6.8 to 3.5, the dissociation ratio is varied to from 99 to 33%.

With a view to confirming the absorption wave-numbers of dissociable lactic acid and nondissociable lactic acid, the infrared absorption spectrum of an 1% lactic acid standard liquid varying the pH thereof from 2 to 7 is shown in FIG. 7.

An equation for obtaining the lactic acid concentration (L)(g/l) was led by selecting a wave-number at 1575 $cm^{-1}$ as an absorption wave-number with a small noise due to impurities and a large relative change for dissociable lactic acid and a wave-number at 1725 $cm^{-1}$ for nondissociable lactic acid and combining amendments of creeping with these two wave-numbers (FIG. 8).

$$L=(0.524 \times A1725+0.476+A1575)/0.00045$$

It has become apparent that the lactic acid concentration can be calculated according to the above equation. Glucose concentrations, lactic acid concentrations and pHs obtained from the infrared absorption spectrum and values measured by the enzyme method and pH electrodes are shown in Table 1. Glucose concentrations and lactic acid concentrations could be calculated from the infrared absorption spectrum measured in-line at a high precision.

For dissociable lactic acid, absorption at 1457 $cm^{-1}$ 1416 $cm^{-1}$, 1362 $cm^{-1}$, 1315 $cm^{-1}$ and 1045 $cm^{-1}$ other than 1575 $cm^{-1}$ can be utilized, and for nondissociable lactic acid, absorption at 1237 $cm^{-1}$ and 1131 $cm^{-1}$ other than 1725 $cm^{-1}$ can be utilized.

TABLE 1

| Values obtained by actual measurements | | | | | | | |
|---|---|---|---|---|---|---|---|
| Culture time (h) | Glucose conc. (g/l) | Lactic acid conc. (g/l) | Titration acidity (ml) | pH | Absorbance/$cm^{-1}$ | | |
| | | | | | 1035 | 1725 | 1575 |
| 0 | 19.80 | 0.50 | 1.8 | 6.45 | 0.02318 | 0.00000 | 0.00042 |
| 4 | 18.47 | 2.07 | 3.1 | 5.92 | 0.02240 | 0.00002 | 0.00190 |
| 6 | 15.70 | 4.70 | 5.4 | 4.77 | 0.02069 | 0.00055 | 0.00390 |
| 8 | 12.93 | 7.32 | 7.6 | 4.25 | 0.01904 | 0.00210 | 0.00458 |
| 10 | 10.33 | 9.50 | 9.5 | 4.00 | 0.01752 | 0.00379 | 0.00487 |
| 15 | 6.17 | 12.60 | 12.1 | 3.73 | 0.01500 | 0.00625 | 0.00510 |
| 19 | 3.64 | 14.83 | 14.0 | 3.64 | 0.01351 | 0.00790 | 0.00526 |
| 27 | 0.40 | 18.06 | 16.8 | 3.53 | 0.01155 | 0.01071 | 0.00527 |

| Values obtained by calculation from absorbance* | | | | |
|---|---|---|---|---|
| Culture time (h) | Glucose conc. (g/l) | Lactic acid conc. (g/l) | Titration acidity (ml) | pH |
| 0 | 19.80 | 0.45 | 1.7 | 6.48 |
| 4 | 18.50 | 2.05 | 3.1 | 5.84 |
| 6 | 15.65 | 4.80 | 5.4 | 4.71 |
| 8 | 12.90 | 7.31 | 7.6 | 4.20 |
| 10 | 10.37 | 9.57 | 9.5 | 3.97 |
| 15 | 6.17 | 12.66 | 12.2 | 3.77 |
| 19 | 3.68 | 14.74 | 13.9 | 3.68 |
| 27 | 0.42 | 18.00 | 16.7 | 3.55 |

*Calculation equations
Glucose concentration=(A1035-0.0113)/0.0006
Lactic acid concentration (g/l)=(0.524×A1725+0.476×A1575)/0.00045
Titration acidity=(Lactic acid concentration claculated from absorbance+1.57)1.17
pH=3.86+log (A1575/A1725)

BEST EMBODIMENTS FOR CARRYING OUT THE INVENTION

Next, the present invention will be described more specifically according to Examples; however, the present invention is restricted to the following Examples by no means.

EXAMPLE 1

Lactobacillus casei was cultured stationary at 37° C. in a logosa medium (J. Inf. Dis., 110, 258–267, 1962). As typical state variables were selected the glucose concentration, the lactic acid concentration and the bacterial concentration. For an infrared spectrum, the continuous automatic in-line measurement of an infrared absorption spectrum was performed within a range of from 1900 to 900 cm$^{-1}$ by a combination of an infrared spectrometer, FT-IR FTS-65A (Bio-Rad Digilab) and an FT-IR probe, ATR Model DPR-210 (S) (A×10 m Analytical). The accumulation and analysis of data were investigated by means of a computer (IBM-PC). With a view to contrasting with an infrared absorption spectrum, the quantitative determination of glucose and lactic acid was performed by the enzyme method. As a result of it, the glucose concentration, the lactic acid concentration, the acidity and the pH value could be measured precisely by the method of the present invention, as described above.

EXAMPLE 2

Figure 1:
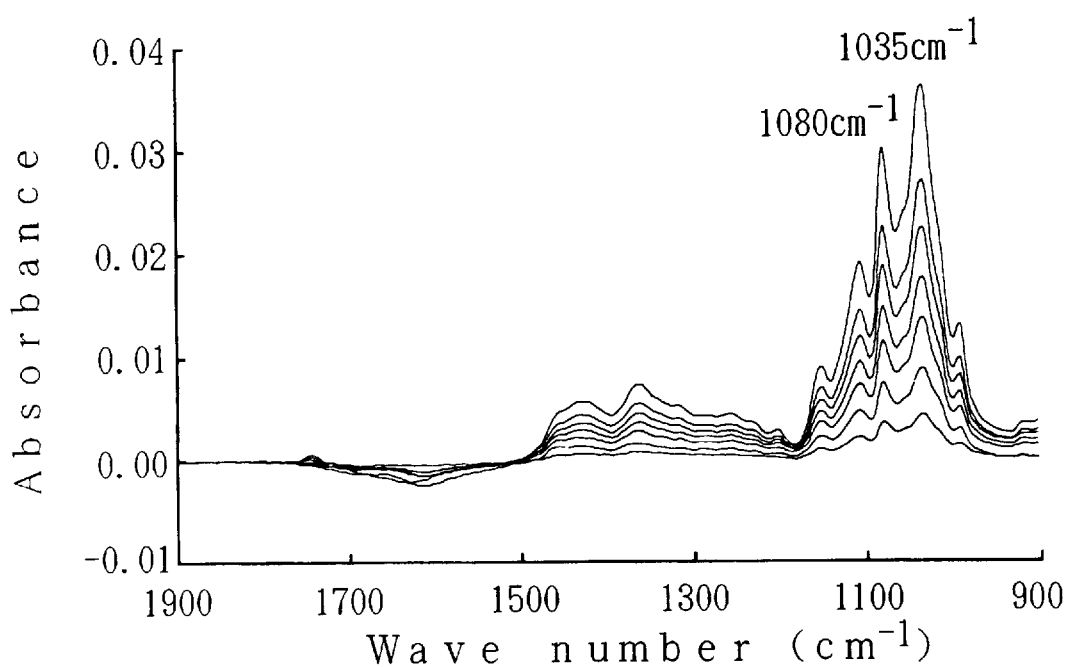
FIG. 1 shows the infrared absorption spectrum of a glucose standard liquid from which the absorption of water is deducted.
Figure 2:
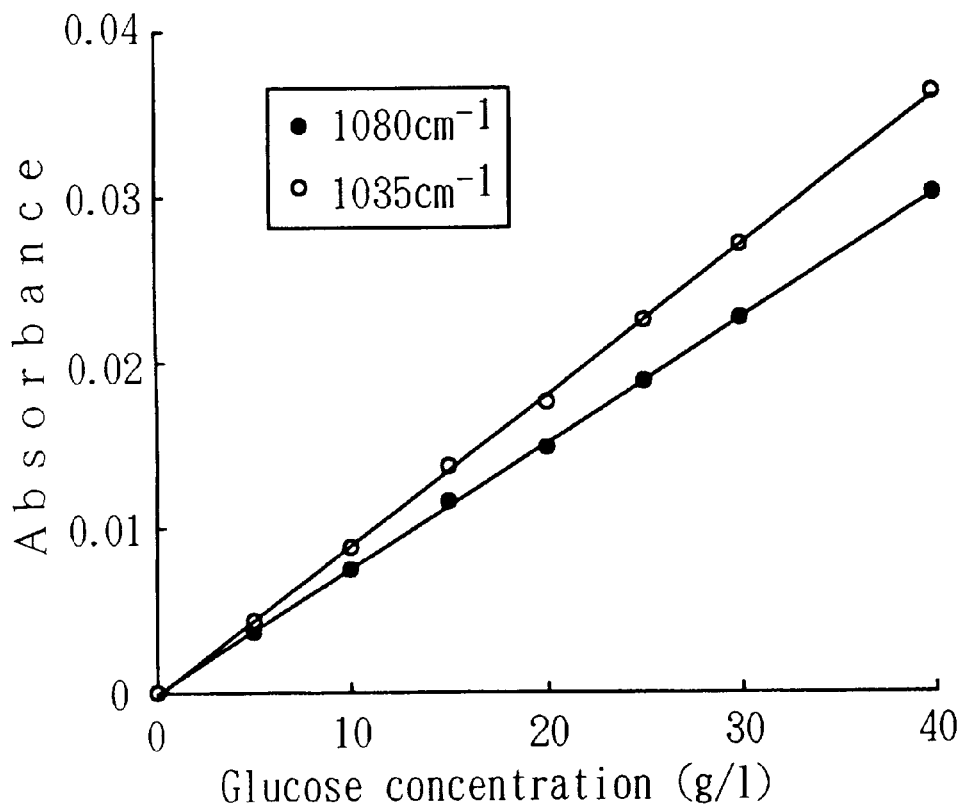
FIG. 2 shows the relation between the absorbance from which the absorption of water is deducted and the glucose concentration.
Figure 3:
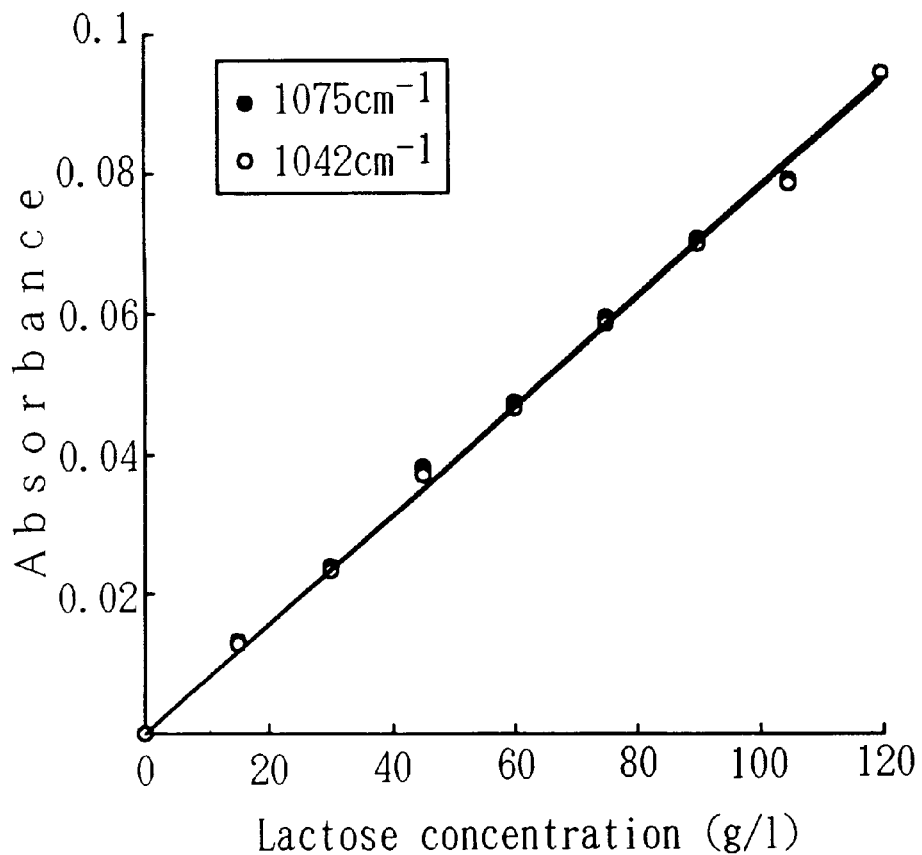
FIG. 3 shows the relation between the absorbance from which the absorption of water is deducted and the lactose concentration.
Figure 4:
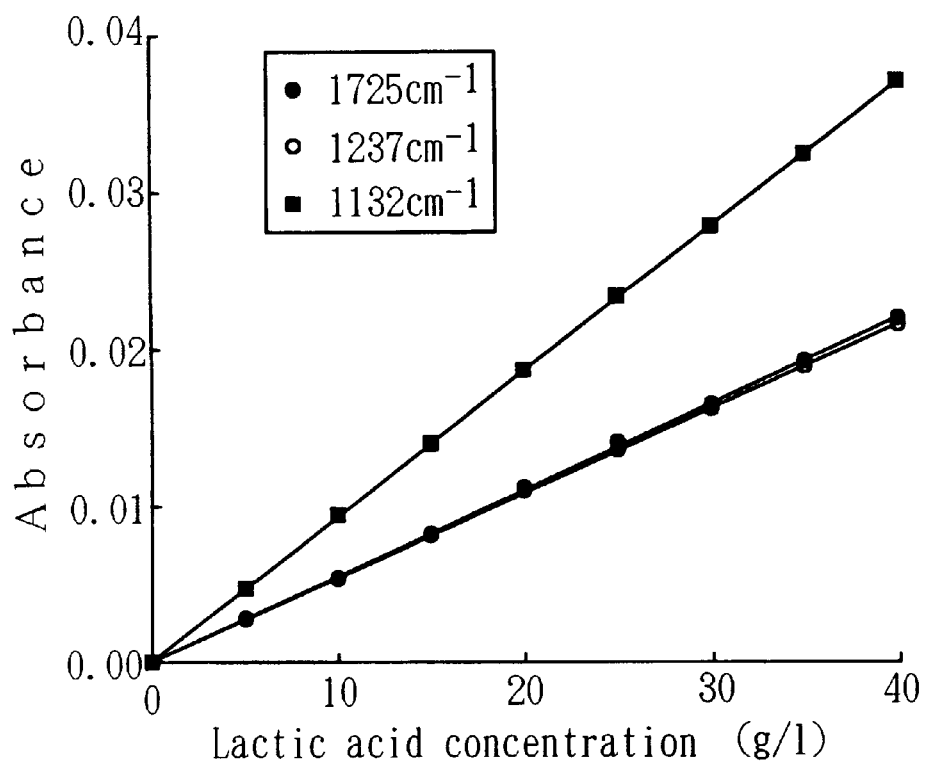
FIG. 4 shows the relation between the absorbance from which the absorption of water is deducted and the lactic acid concentration.
Figure 5:
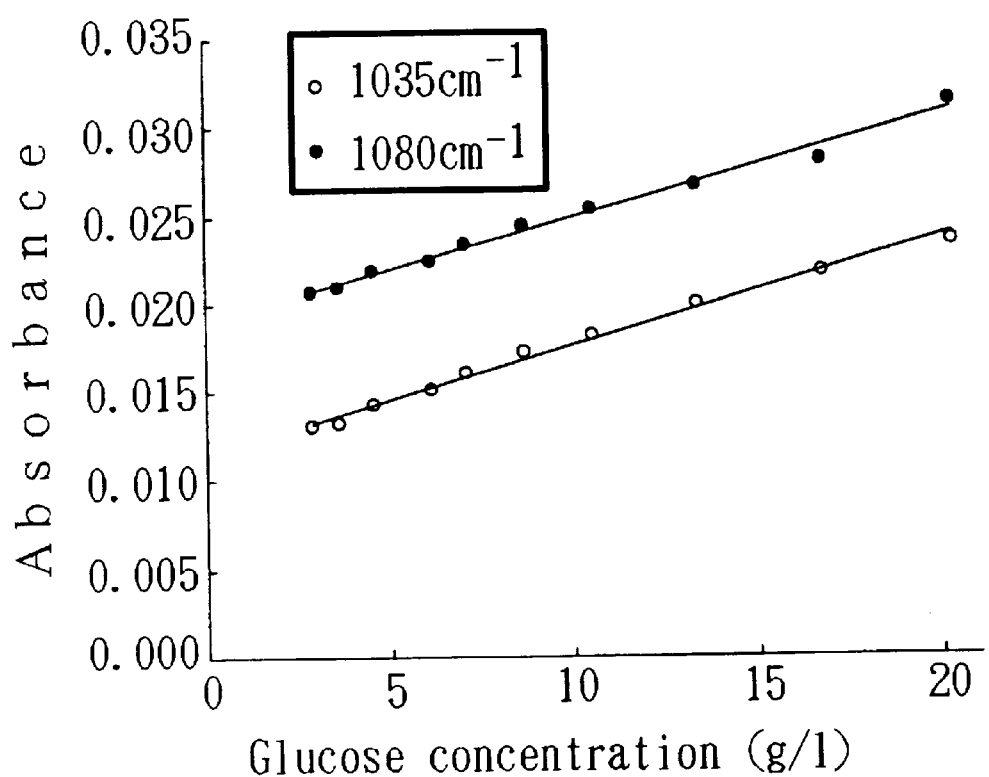
FIG. 5 shows the relation between the glucose concentration and the absorbance in Example 1.
Figure 6:
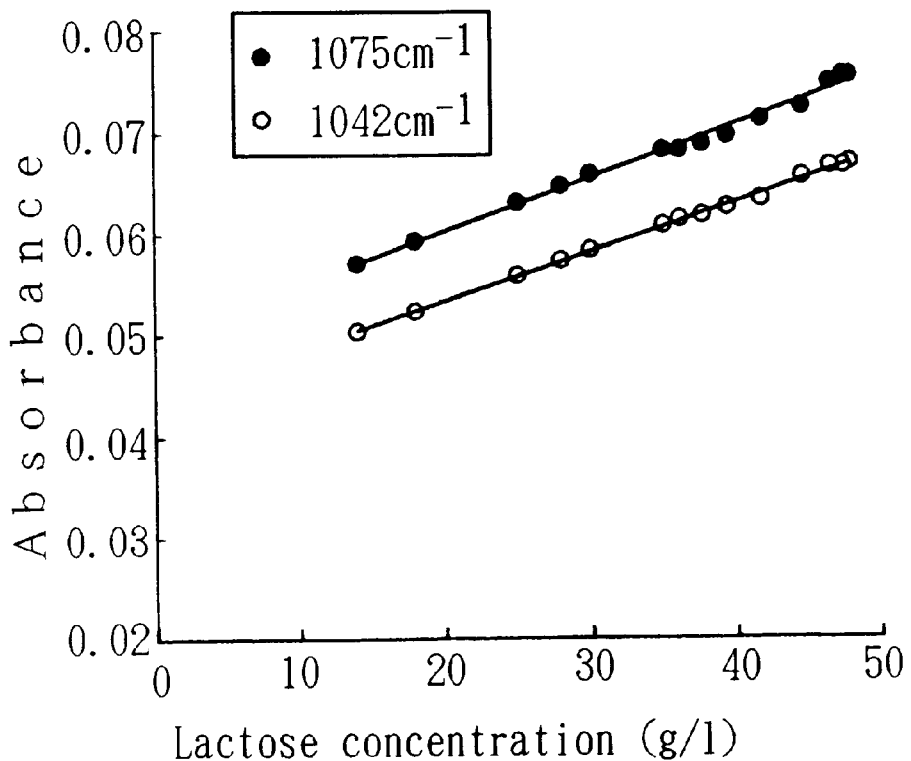
FIG. 6 shows the relation between the lactose concentration and the absorbance in Example 2.
Figure 7:
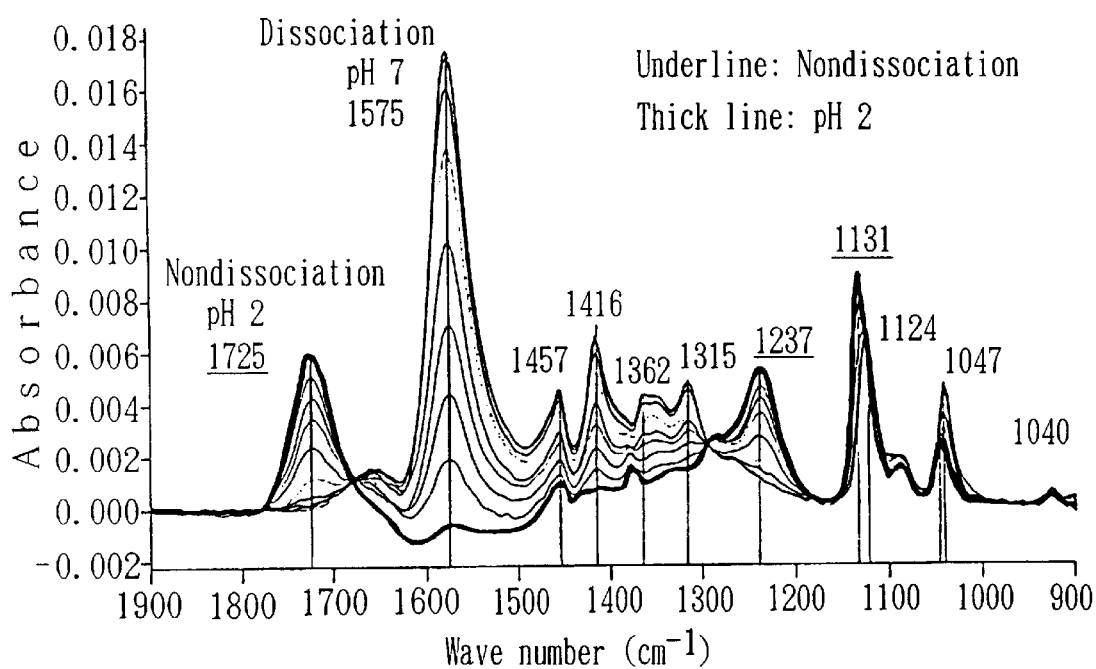
FIG. 7 shows the infrared absorption spectrum of a 1% lactic acid solution with a pH of from 2 to 7 from which the absorption of water is deducted.
Figure 8:
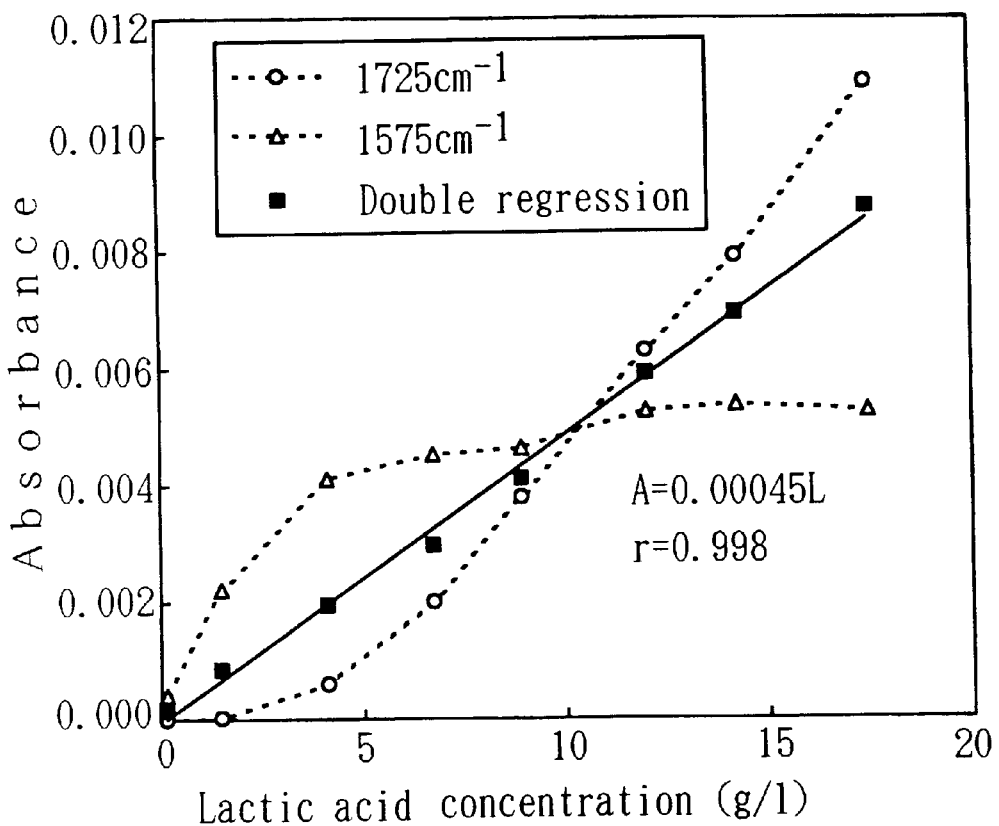
FIG. 8 shows the relation between the lactic acid concentration in a logosa medium and the infrared absorbance of dissociable and nondissociable lactic acid from which that of culture time 0 is deducted.
Figure 9:
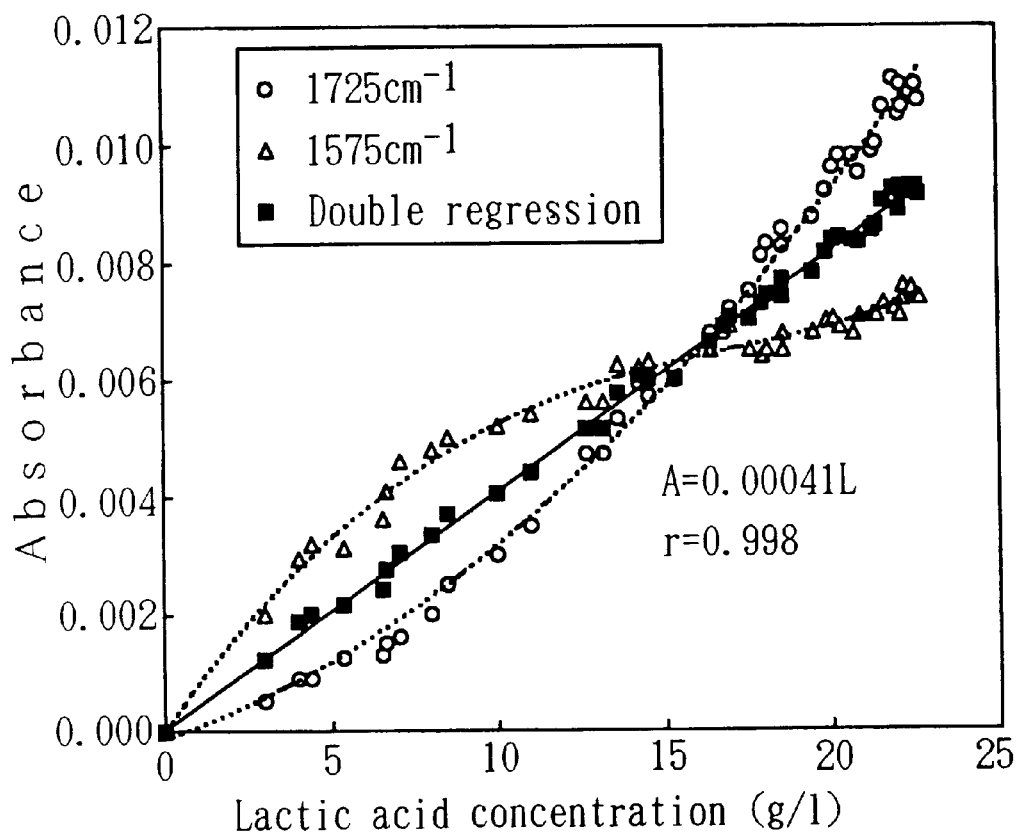
FIG. 9 shows the relation between the lactic acid concentration in a milk medium and the infrared absorbance of dissociable and nondissociable lactic acid from which that of culture time 0 is deducted.

Replacing the logosa medium with a milk medium, the measurement of lactic acid showing a high correlation with titration acidity, a typical state variable of lactic bacteria fermented milk by the infrared spectrometry was performed and investigated in the same manner as in Example 1. It has become apparent, as a result of it, that the lactic acid concentration (L) (g/l) can be calculated from the infrared absorbance (A1725, A1575) at 1725 cm$^{-1}$ and 1574 cm$^{-1}$ according to the following equation (FIG. 9):

$$L=(0.524 \times A1725 + 0.476 \times A1575)/0.00041$$

Even in the milk medium with a high viscosity and adhesion, the quantitative determination of typical state variables could be performed by the method of in-line measurement wherein a probe of an infrared absorption spectrum measuring device was fixed directly to a fermentation tank. Hence, it has become apparent that the method of the present invention is extremely effective in the systems of fermented milk drinks and fermented milk, though the culture processes of them have been monitored and controlled by titration acidity conventionally.

As described above in detail, the present invention is a method for controlling culture of lactic bacteria, characterized in that the method comprises measuring, in the step of cultivating lactic bacteria, the intensity of the infrared absorption assignable to dissociable lactic acid and that of the infrared absorption assignable to nondissociable lactic acid in the culture, the intensity of the infrared absorption assignable to an alcoholic C-O group of glucose and/or that of the infrared absorption assignable to an alcoholic C-O group of lactose directly by the FT-IR spectrometry, respectively, and calculating the pH value of the culture and/or the lactic acid concentration of the culture on the basis of these measurements, and that further calculating the glucose concentration or the lactose concentration; according to the present invention, it becomes possible to measure various index values needed for controlling the step of cultivation in a rapid, simple and precise manner in the production of products utilizing lactic bacteria such as fermented milk, and thereby to monitor and control the state of culture of lactic bacteria in the step of cultivation in a simple and rapid manner. In addition, it becomes possible by employing the ATR-FT-IR spectrometry to perform the measurement of the above various index values in-line and to control the step of culture of lactic bacteria automatically.

What is claimed is:

1. A method for measuring pH of culture of lactic bacteria, which comprises measuring, in the step of cultivating lactic bacteria, the intensity of the infrared absorption assignable to dissociable lactic acid and that of the infrared absorption assignable to nondissociable lactic acid in the culture by the FT-IR spectrometry, and calculating the pH value of the culture according to these measurements.

2. A method for measuring pH of culture of lactic bacteria as claimed in claim 1, characterized in that the intensity of the infrared absorption is measured in-line by the ATR-FT-IR spectrometry.

3. A method for measuring pH of culture of lactic bacteria as claimed in claim 1, characterized in that the intensity of the infrared absorption assignable to dissociable lactic acid is the intensity of the infrared absorption at about 1575 cm$^{-1}$ and the intensity of the infrared absorption assignable to nondissociable lactic acid is the intensity of the infrared absorption at about 1725 cm$^{-1}$.

* * * * *